United States Patent
Imeson

(10) Patent No.: US 11,975,147 B2
(45) Date of Patent: May 7, 2024

(54) CURVED BOUGIE GUIDE

(71) Applicant: Shale Imeson, Stockton, CA (US)

(72) Inventor: Shale Imeson, Stockton, CA (US)

( * ) Notice: Subject to any disclaimer, the term of this patent is extended or adjusted under 35 U.S.C. 154(b) by 709 days.

(21) Appl. No.: 17/154,404

(22) Filed: Jan. 21, 2021

(65) Prior Publication Data

US 2021/0213222 A1 Jul. 15, 2021

Related U.S. Application Data

(63) Continuation of application No. PCT/US2020/040496, filed on Jul. 1, 2020.

(60) Provisional application No. 62/872,848, filed on Jul. 11, 2019.

(51) Int. Cl.
*A61M 16/04* (2006.01)

(52) U.S. Cl.
CPC ..... *A61M 16/049* (2014.02); *A61M 2205/582* (2013.01); *A61M 2205/583* (2013.01)

(58) Field of Classification Search
CPC .............. A61M 16/04; A61M 16/0488; A61M 16/049; A61M 16/0497; A61M 2205/582; A61M 2205/583
See application file for complete search history.

(56) References Cited

U.S. PATENT DOCUMENTS

| | | | |
|---|---|---|---|
| 6,874,504 B1 | 4/2005 | Raspallo | |
| 8,161,967 B2 | 4/2012 | Harms | |
| 8,631,795 B1 | 1/2014 | McMurray | |
| 8,663,099 B2 | 3/2014 | Tydlaska | |
| 10,596,339 B2 * | 3/2020 | Musuku | A61M 16/0415 |
| 10,653,307 B2 * | 5/2020 | Molnar | A61B 1/018 |
| 11,051,682 B2 * | 7/2021 | Molnar | A61B 1/00103 |
| 11,464,403 B2 * | 10/2022 | Hara | A61B 1/267 |
| 11,638,797 B2 * | 5/2023 | Meadows | A61M 16/0488 |
| | | | 128/207.15 |
| 11,684,737 B2 * | 6/2023 | Avniel | A61M 16/0463 |
| | | | 128/207.14 |
| 2010/0261967 A1 | 10/2010 | Pacey | |
| 2012/0178997 A1 * | 7/2012 | Tydlaska | A61B 1/0676 |
| | | | 600/188 |

(Continued)

FOREIGN PATENT DOCUMENTS

| | | |
|---|---|---|
| CN | 105797253 A | 7/2016 |
| GB | 2454018 A | 4/2009 |

(Continued)

OTHER PUBLICATIONS

European Patent Office (EPO), Communication (Extended European Search Report) dated Jun. 28, 2023, related European patent application No. 20836903.3, pp. 1-10, claims searched, 11-15.

(Continued)

*Primary Examiner* — Joshua Lee
(74) *Attorney, Agent, or Firm* — O'BANION & RITCHEY LLP; John P. O'Banion

(57) ABSTRACT

A guide, system and method for endotracheal intubation using a pre-shaped, curvilinear guide to deliver a flexible bougie into the trachea under videoscopic visualization. The guide comprises an elongate tube with sufficient rigidity to maintain a pre-shaped path with multiple curvatures to provide a conduit through which the bougie is passed to the proper location and orientation with respect to the glottis and upper trachea.

19 Claims, 4 Drawing Sheets

(56) References Cited

U.S. PATENT DOCUMENTS

| | | | |
|---|---|---|---|
| 2012/0298112 A1 | 11/2012 | Paskar | |
| 2016/0081539 A1* | 3/2016 | Pagan | A61B 1/00154 600/184 |
| 2016/0166791 A1* | 6/2016 | Kleene | A61M 16/0488 600/188 |
| 2017/0157349 A1 | 6/2017 | Gao | |
| 2017/0325667 A1* | 11/2017 | Alonso Babarro | A61M 16/0488 |
| 2018/0133422 A1* | 5/2018 | Olympio | A61M 16/049 |
| 2018/0326629 A1* | 11/2018 | Miller | B29C 45/1679 |
| 2019/0014980 A1* | 1/2019 | Herskovic | A61M 16/0488 |
| 2019/0059710 A1* | 2/2019 | Molnar | A61B 1/2676 |
| 2019/0125177 A1* | 5/2019 | Sutherland | A61B 1/0014 |
| 2019/0151586 A1* | 5/2019 | Schmitz | A61M 16/0488 |
| 2019/0351167 A1* | 11/2019 | Musuku | A61H 7/00 |
| 2019/0380569 A1* | 12/2019 | Hara | A61M 16/04 |
| 2020/0030558 A1* | 1/2020 | Avniel | A61M 16/049 |
| 2020/0113427 A1* | 4/2020 | Molnar | A61B 90/361 |
| 2020/0206445 A1* | 7/2020 | Musuku | A61M 16/0445 |
| 2020/0297958 A1* | 9/2020 | Meadows | A61M 16/0488 |
| 2020/0338291 A1* | 10/2020 | Ananthanarayanan | A61M 16/0434 |

FOREIGN PATENT DOCUMENTS

| | | |
|---|---|---|
| GB | 2542640 A | 3/2017 |
| WO | 201112677 A1 | 2/2011 |
| WO | 2018094015 A | 5/2018 |
| WO | 2019222196 A1 | 11/2019 |

OTHER PUBLICATIONS

Sunmed, "Oropharyngeal Airway Williams Airway", 2019 SunMed, 2710 Northridge Drive NW, Grand Rapids, MI 49544 USA, 3 pages, downloaded from https://sun-med.com/product/detail/williams-airway.

ISA/US, United States Patent and Trademark Office, International Search Report and Written Opinion dated Sep. 21, 2020, related PCT international application No. PCT/US2020/040496, pp. 1-9, claims searched, pp. 10-14.

* cited by examiner

US 11,975,147 B2

CURVED BOUGIE GUIDE

CROSS-REFERENCE TO RELATED APPLICATIONS

This application claims priority to, and is a 35 U.S.C. § 111(a) continuation of, PCT international application number PCT/US2020/040496 filed on Jul. 1, 2020, incorporated herein by reference in its entirety, which claims priority to, and the benefit of, U.S. provisional patent application Ser. No. 62/872,848 filed on Jul. 11, 2019, incorporated herein by reference in its entirety. Priority is claimed to each of the foregoing applications.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to patient endotracheal intubation assistance devices, and more particularly to patient endotracheal intubation via guided delivery of a bougie.

2. Background Discussion

Clinicians (primarily anesthesiologists, intensivists, and emergency medicine physicians) have long used direct laryngoscopy to visualize the glottis (opening to the trachea that includes the vocal cords) in order to perform endotracheal intubation. This procedure requires much practice, is challenging to perform, and in some patients can be impossible even in expert hands. Rarely, the consequences of failure can include brain damage and death. Over the years numerous techniques have been developed to improve our odds of success, but no technique or combination of techniques has proven 100% reliable, even in patients with apparently normal airway anatomy. One such technique that has recently become widely available is video laryngoscopy. With this technique the odds of successfully visualizing the glottis approach 100%. However, visualization does not guarantee successful endotracheal intubation.

Guiding the endotracheal tube into the glottis can be challenging even when visualization is excellent. The most reliable video laryngoscope blades (the part of the instrument that pushes the tongue anteriorly and out of the line of vision) are hyperangulated. At times the angle of approach to the glottis is so anterior that the endotracheal tube tip, even when a stylet (a thick, stiff wire placed inside the endotracheal tube) designed to match the "hyper" angle of the blade is used, the tube cannot be slipped beyond the vocal cords.

A soft, non-malleable device called a bougie is sometimes used to aid guidance of the endotracheal tube into the trachea. While a bougie may have numerous uses in medicine, they are typically used to widen a passageway or guide another instrument into a passageway. The bougie is somewhat easier to pass between the vocal cords since it is smaller and easier to manipulate than the endotracheal tube. However, it is likely to be ineffective during video laryngoscopy since it is not stiff enough to hold a curved shape. A stiffer, malleable bougie exists but passing it into the trachea risks potentially fatal injury to the trachea or deeper airways.

BRIEF SUMMARY

An aspect of the present description is a guide apparatus, system and method for endotracheal intubation using a pre-shaped, curvilinear guide to deliver a flexible (atraumatic) bougie into the trachea under videoscopic visualization. The guide serves as a conduit through which the bougie is passed. The system and method is proven easy, quick and effective. The technique is intuitive and needs little to no special training for anyone proficient in the use of video laryngoscopy for endotracheal intubation.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

FIG. 1 through FIG. 5 illustrate embodiments of a guide apparatus, system and method for endotracheal intubation using a pre-shaped, curvilinear guide to deliver a flexible (atraumatic) bougie into the trachea under videoscopic visualization.

Figure 1:
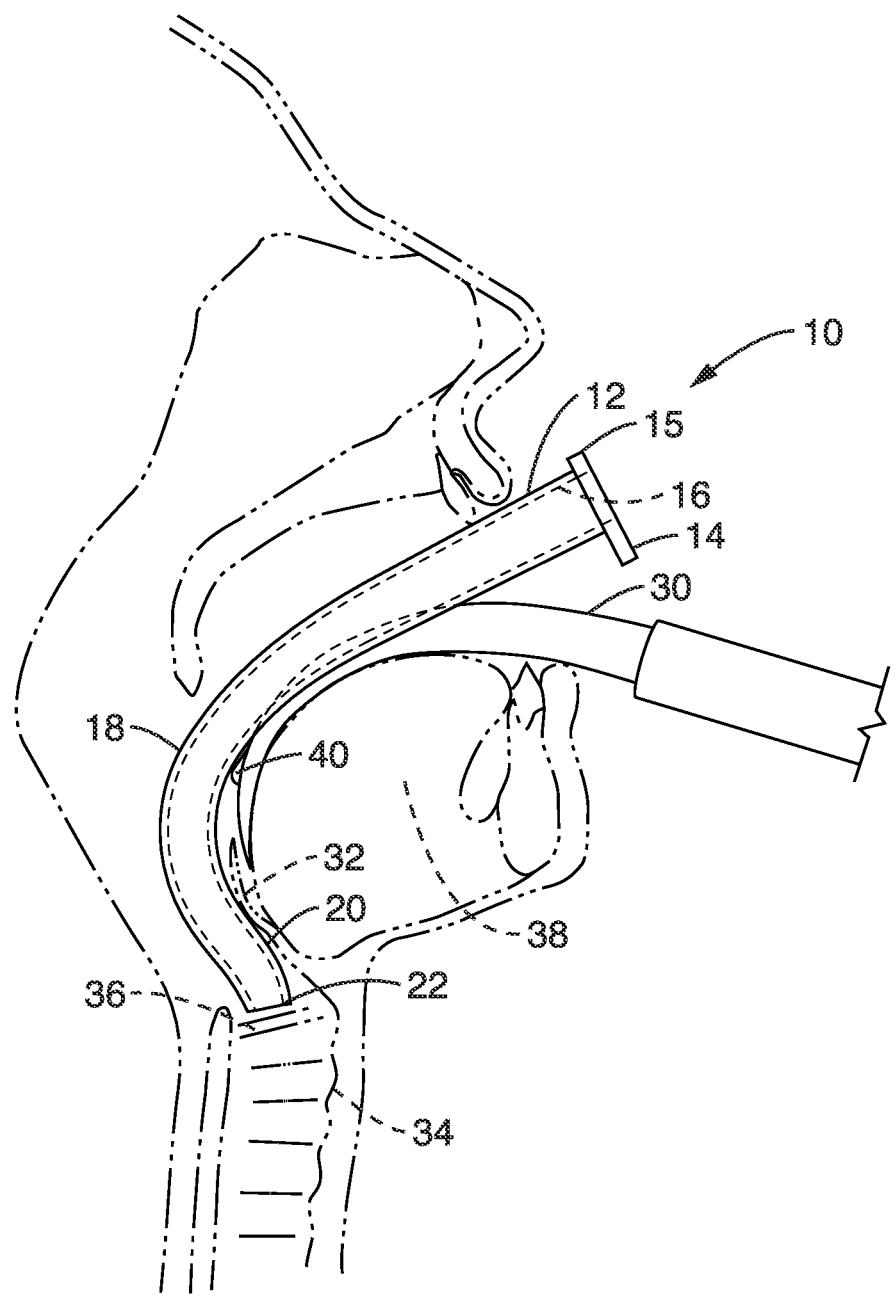
FIG. 1 shows a schematic side view of a bougie guide in accordance with the present description installed into the trachea of a patient along with a video laryngoscope blade.

Referring to FIG. 1, an embodiment of a bougie guide apparatus 10 in accordance with the present description is shown installed in glottis 36 for access of the trachea 34 after placement of a video laryngoscope blade 30. The video laryngoscope blade 30 acts to push the tongue 38 anteriorly and out of the line of vision, and the distal tip of the blade 30 is configured to curve around the tongue 38 to the epiglottis 32. The distal end of the blade 30 comprises a camera 40 for visualization of the patient anatomy and glottis 36.

In the embodiment shown the bougie guide 10 comprises an elongate tube 12 having a collar 14 at its proximal end, with the tube 12 having a tapered, curved shape terminating at distal end 22. The tube 12 comprises a central aperture 16 that extends from the collar 14 at the proximal end to the distal end 22 for passage of a bougie.

The tube 12 comprises a primary or first curvature 18 that is sized and angled to follow the path of blade 30 at least partially along its length. However, as shown in FIG. 1, the orientation of the blade 30 is hyperangulated with respect to the glottis 36 and trachea 34, such that the angle of approach of a tube merely matching its path would place and/or orient the bougie too far anterior within the patient, thus creating problems for the bougie and endotracheal tube to be positioned beyond the vocal cords and glottis 36.

To accommodate these anatomical difficulties, the tube 12 comprises a second curvature 20 that is distal to first curvature 18. The second curvature 20 reverses course of the first curvature 18 to form a subtle "s" shape that positions and orients the distal end 22 of the guide 10 at the glottis 36, preferably at an angle substantially aligned with path of the trachea 34.

Figure 2:
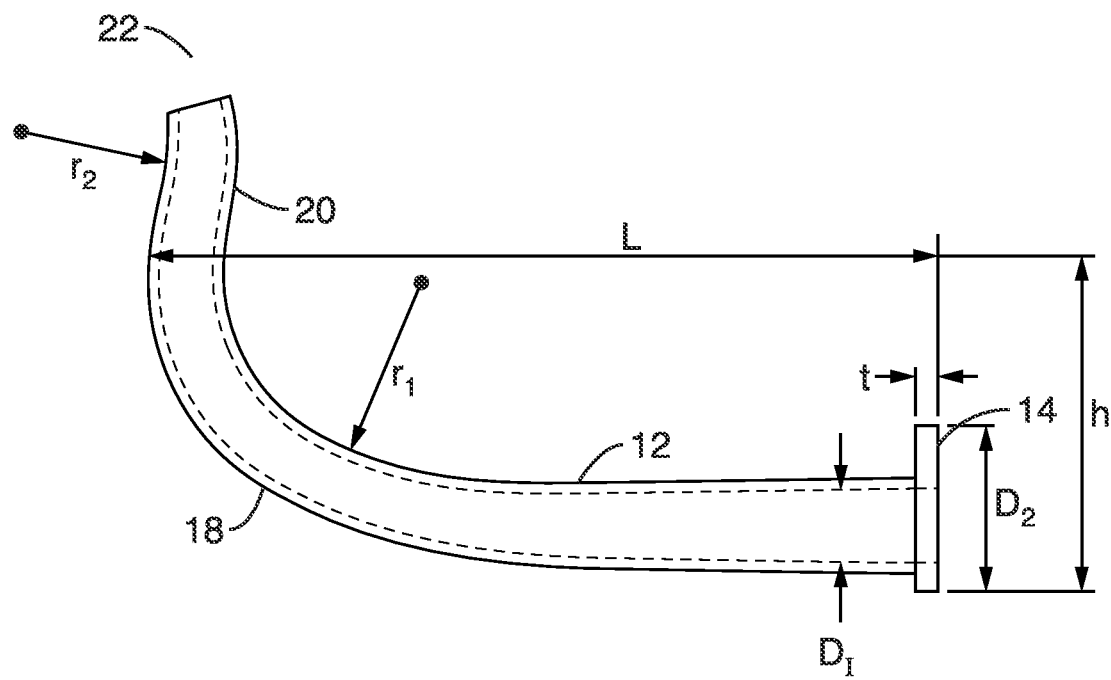
FIG. 2 shows a side view of the bougie guide of FIG. 1.
Figure 3:
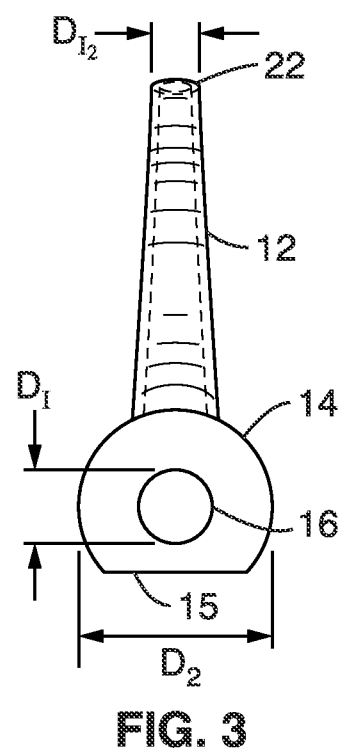
FIG. 3 shows a front view of the bougie guide of FIG. 1.

FIG. 2 and FIG. 3 show side and front views, respectively, of the bougie guide 10 in detail. Elongate tube 12 comprises a circular cross-section that tapers from the proximal end, with an internal diameter $D_1$ that is larger than the diameter $D_{12}$ at the distal end 22. In one embodiment, internal diameter $D_1$ of central aperture 16 is approximately 15 mm at the collar 14, and the internal diameter $D_{12}$ is approximately 7 mm.

In the embodiment shown in FIG. 2 the tube 12 has a straight section that slopes slightly from the collar 14, and leads into first curvature 18 having a radius $r_1$ that is generally larger than second curvature 20 having radius $r_2$. The curvature leading through $r_1$ is generally configured to follow the natural curvature of the tongue 38, (approximately 95° to 105°). While curvatures 18 and 20 are shown having a radius, it is appreciated that curvatures 18 and 20 may comprise any curvilinear shape or path.

The collar 14 is generally circular in shape, having a thickness t of approximately 3 mm, and diameter $D_2$ of approximately 25 mm. The collar 14 has a thumb notch 15 to help with administering and/or rotating the guide 10, and as well providing a tactile (and visual) indicator or clocking of the rotational position of the guide 10 in the patient.

In one embodiment the overall length L of the guide 10 is approximately 130 mm, and the height h is approximately 60 mm.

It is appreciated that all dimensions are provided for illustrative purposes only, and that sizing and variations in orientation and shape may be employed to match certain patients (e.g. a bougie guide 10 may have smaller dimensions for small patients/children).

The overall length L of the guide 10 is sized so that the distal end 22 can extend to or past the glottis 36 while the collar 14 at the proximal end is external to the patient's mouth to allow for ease of manipulation from outside the mouth and optimal positioning options. The round profile of tube 12, along with notch 15 in collar 14, allow for easy rotation within the oropharynx when guiding the distal end 22 of tube 12 to the target location. The wall thickness of the tube 12 is generally about 1 mm to 3 mm, with sufficient material for rigidity to maintain its preformed curvature, while also being slightly compliant to deflect when necessary.

In a preferred embodiment, the tube 12 is constructed from a non-reflective dark-colored plastic that minimizes videoscopic glare. While any number of materials may be selected, the tube 12 is comprised of a generally semi-rigid to rigid material or construction to hold its shape, with inner and outer surfaces having a "slippery" or low-friction texture configured to easily glide into the oropharynx and with respect to the bougie without resistance. A biocompatible coating may be applied to inner and outer surfaces of tube 12 to minimize friction between anatomy and components. In a preferred configuration the guide 10 is single use.

Figure 4:
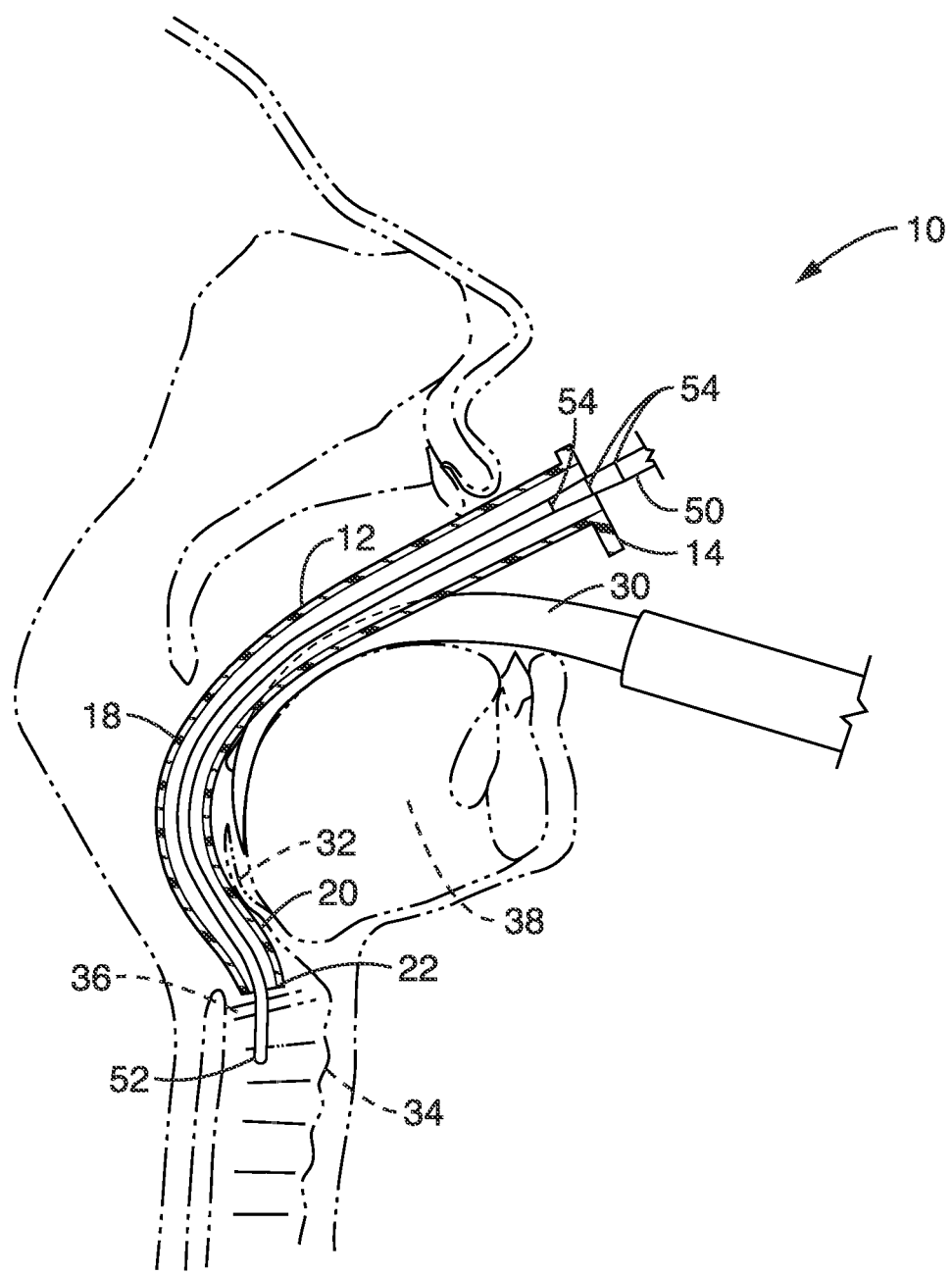
FIG. 4 is a schematic side-section view of the bougie guide of FIG. 1 with a distal end of a bougie being delivered into the trachea.
Figure 5:
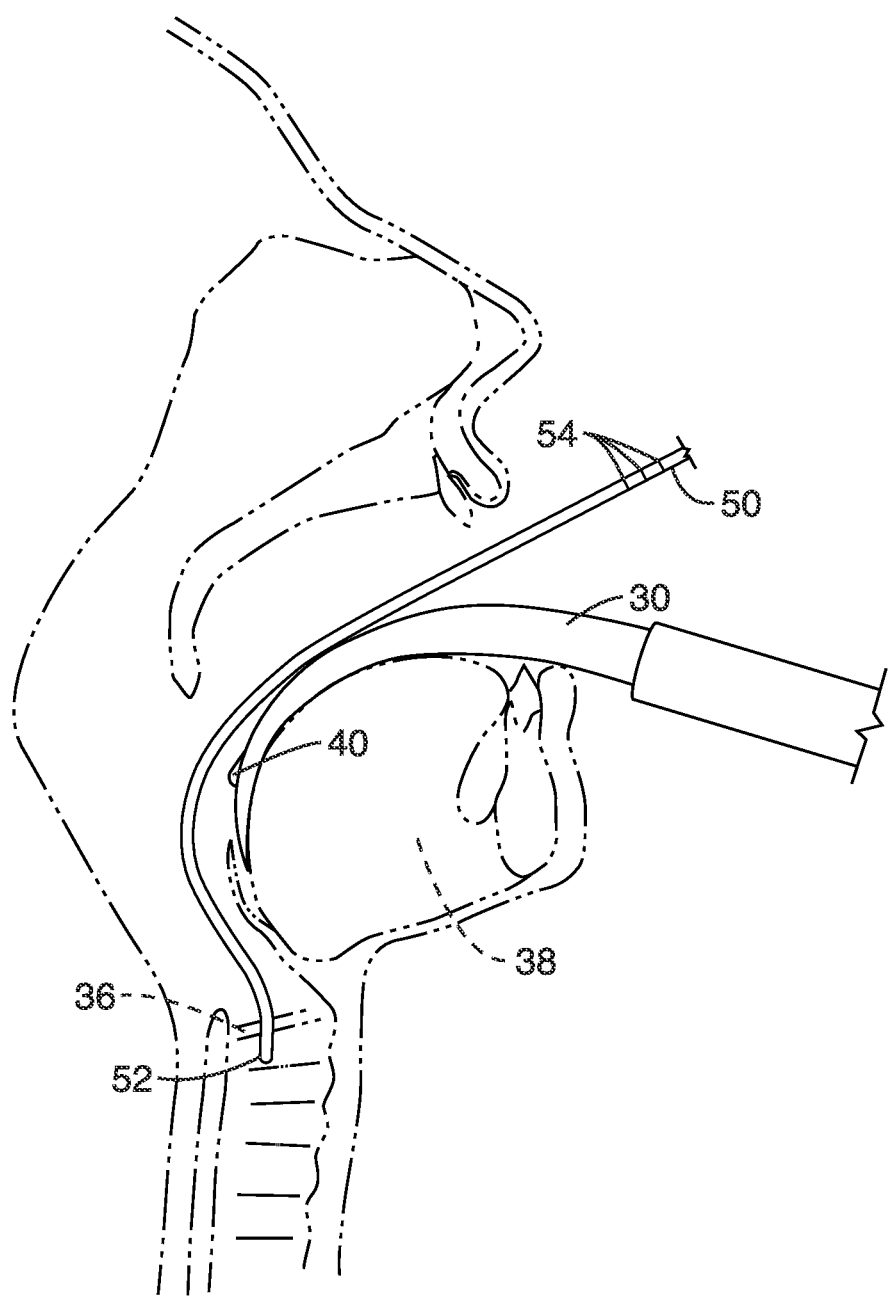
FIG. 5 is a side view of the bougie guide of FIG. 1 removed to leave the distal end of a bougie at the desired location in the trachea.

A preferred method for endotracheal intubation using the pre-shaped, curvilinear bougie guide 10 of the present description is detailed in FIG. 1, FIG. 4 and FIG. 5.

As seen in FIG. 1, a video laryngoscope blade 30 is inserted into the patient's mouth and advanced such that the distal tip of the blade 30 curves around the tongue 38 and lodges anterior to the epiglottis 32. This acts to push the tongue 38 anteriorly and out of the line of vision. Visualization of the oropharynx is achieved with camera 40.

Next, the distal end 22 of the bougie guide 10 is inserted in the patient's mouth and manually advanced through the oropharynx along the path of the blade 30. The collar 14 and thumb notch 15 provide manual purchase at the proximal end of the guide 10 for both translation and rotation of the tube 12 when guiding the distal end 22 of tube to the target location. Slight clockwise or counterclockwise rotation of the tube 12 can affect the curvature of the tube in the mouth, as well as position and orientation of the distal end 22 of the tube 12 to advance past tight anatomy, preferably with aid of videoscopic visualization via camera 40. The flat of the thumb notch 15 also serves as a rotational reference point for the physician while installing the guide 10.

FIG. 4 is a schematic side-section view of the bougie guide 10 with a distal end 52 of a bougie 50 being delivered into the trachea 34. The bougie 50 is preferably sized with sufficient length, diameter and flexibility to navigate through the length of the tube 12. One exemplary bougie configuration is 15 Fr×70 cm with Coude tip (e.g. model 9-0212-70 by SunMed (www.sun-med.com). With the distal end 22 of the guide 10 installed at the target location at the glottis 36, the flexible (atraumatic) bougie 50 is inserted in aperture 16 at the proximal collar 14 and advanced along the length of the tube 12. The taper of the tube 12 with the larger diameter at the proximal end 14 allows for easy advancement through the mouth, (promoting for less friction where the anatomy is more "open") and then constricts to a smaller diameter when the anatomy becomes more tight, while still having an inner diameter $D_{12}$ to allow for sufficient passage of the bougie 50.

When the distal end 52 of a bougie 50 reaches distal end 22 of the guide 10, it is positioned at the glottis 36 and lined up with the trachea 34 (as a result of the curvatures 18/20 in the tube 12) so that it easily passes through vocal folds of the glottis 36 and into the trachea 34. Placement of the distal end 52 may be verified under videoscopic visualization.

In addition to or as alternative to visualization, the bougie 50 may comprise a series of bands or markers 54 corresponding to the length along the aperture 16 of the guide tube 12, which provides visualization that the distal end 52 of a bougie 50 is approaching, at or past the distal end 22 by some increment. For example, when a first marker 54 is approaching the collar 14, the physician is alerted that the distal end 52 is about to exit the guide at end 22. The bougie can then be advanced a specified distance (e.g., 30 mm) past the distal end 22 corresponding to aligning one or more of the indicators 54 with the collar 14.

Referring now to FIG. 5, once the distal end 52 of a bougie 50 is at the desired location within the trachea 34, the guide 10 is retracted along the path of the bougie 50 while the bougie is held in place to leave the distal end 52 of a bougie at the desired location in the trachea 34. The endotracheal tube (not shown) is then advanced over the bougie 50 into the trachea 34 to intubate the patient. Removing the guide 10 from the mouth prior to passing the endotracheal tube over the bougie and into the trachea minimizes risk of traumatic injury from the device to the mouth, larynx, or associated nerves.

From the description herein those skilled in the art readily will appreciate that the bougie guide can be adapted for various uses. For example, by attaching the appropriate adaptor to the proximal end of the guide, the guide may be connected to an oxygen source, such as a breathing circuit, in order to insufflate supplemental oxygen into the hypopharynx. This may be especially useful during the process of awake intubation. Another example is that, by inserting the distal tip of the guide through the glottic opening and into the upper trachea, positive pressure ventilation may be applied for the purpose of temporary rescue during critical, unplanned loss of airway and ventilation. The guide may be attached to a breathing circuit or other source of positive pressure ventilation for use in such an emergency. Accordingly, the guide provides versatility of use and can facilitate various treatment protocols.

From the description herein, it will be appreciated that the present disclosure encompasses multiple embodiments which include, but are not limited to, the following:

1. An apparatus for endotracheal intubation of a patient via a flexible bougie, the apparatus comprising: an elongate tube having a distal and proximal end; the elongate tube having a central aperture sized to receive a flexible bougie; the tube being sized to allow insertion in a patient's mouth and advancement through an oropharynx region of the patient such the distal end is located at or near a glottis of the patient while the proximal end is at or outside the patient's mouth; wherein the elongate tube comprises a pre-formed curvilinear path corresponding to a natural curvature around a tongue region of the patient; the natural curvature having a first proximal curvilinear path corresponding to the tongue region and a second curvilinear path distal to and extending in a direction opposite the first curvilinear path to position and orient the distal end of the elongate tube at the glottis and in substantial alignment with a path of a tracheal segment distal of the glottis.

2. The apparatus, system or method of any preceding or following embodiment, wherein the proximal end comprises a circular collar with a thumb notch allowing for manual purchase of the proximal end for advancement and rotation of the elongate tube within the oropharynx region.

3. The apparatus, system or method of any preceding or following embodiment, wherein the notched circular collar provides visual and tactile indication of the angular orientation of the elongate tube with respect to the patient.

4. The apparatus, system or method of any preceding or following embodiment, wherein the elongate tube has a round cross-section that promotes rotation of the tube within the patient and tapers so that the central aperture is larger at the proximal end and smaller at the distal end.

5. The apparatus, system or method of any preceding or following embodiment, wherein the first proximal curvilinear path comprises a first radius and the second curvilinear path comprises a second radius smaller than the first radius.

6. The apparatus, system or method of any preceding or following embodiment, wherein the elongate tube has sufficient rigidity and the second curvilinear path is shaped with respect to the first curvilinear path such that the distal end naturally positions itself at a proper anterior-posterior location with respect to the glottis and such that an exit path of a distal end of the bougie when advanced past the distal end of the elongate tube is aligned with an opening of the glottis and orientation of the trachea.

7. The apparatus, system or method of any preceding or following embodiment, wherein the elongate tube comprises a non-reflective dark-colored plastic configured to minimizes videoscopic glare.

8. A system for endotracheal intubation of a patient, the system comprising: a guide comprising an elongate tube having a distal, proximal end and central aperture therebetween; and a flexible bougie sized with sufficient length, diameter and flexibility to navigate through the central aperture of elongate tube; the elongate tube being sized to allow insertion in a patient's mouth and advancement through an oropharynx region of the patient such the distal end is located at or near a glottis of the patient while the proximal end is at or outside the patient's mouth; wherein the elongate tube comprises a pre-formed curvilinear path corresponding to a natural curvature around a tongue region of the patient; the natural curvature having a first proximal curvilinear path corresponding to the tongue region and a second curvilinear path distal to and extending in a direction opposite the first curvilinear path to position and orient the distal end of the elongate tube at the glottis and in substantial alignment with a path of a tracheal segment distal of the glottis.

9. The apparatus, system or method of any preceding or following embodiment, wherein the proximal end comprises a circular collar with a thumb notch allowing for manual purchase of the proximal end for advancement and rotation of the elongate tube within the oropharynx region.

10. The apparatus, system or method of any preceding or following embodiment, wherein the notched circular collar provides visual and tactile indication of the angular orientation of the elongate tube with respect to the patient.

11. The apparatus, system or method of any preceding or following embodiment, wherein the elongate tube has a round cross-section that promotes rotation of the tube within the patient and tapers so that the central aperture is larger at the proximal end and smaller at the distal end.

12. The apparatus, system or method of any preceding or following embodiment, wherein the first proximal curvilinear path comprises a first radius and the second curvilinear path comprises a second radius smaller than the first radius.

13. The apparatus, system or method of any preceding or following embodiment, wherein the elongate tube has sufficient rigidity and the second curvilinear path is shaped with respect to the first curvilinear path such that the distal end naturally positions itself at a proper anterior-posterior location with respect to the glottis and such that an exit path of a distal end of the bougie when advanced past the distal end of the elongate tube is aligned with an opening of the glottis and orientation of the trachea.

14. The apparatus, system or method of any preceding or following embodiment, wherein the elongate tube comprises a non-reflective dark-colored plastic configured to minimizes videoscopic glare.

15. The apparatus, system or method of any preceding or following embodiment: wherein the bougie comprises one or more markers at a location along its length corresponding to the length along the central aperture of the elongate tube;

and wherein the one or more markers provide visualization that the distal end of a bougie is near, at or past the distal end of the elongate tube by some increment.

16. A method for endotracheal intubation of a patient using a pre-shaped, curvilinear guide via a flexible bougie under videoscopic visualization, the method comprising: delivering a video laryngoscope blade to a location within an oropharynx region of the patient; delivering a curvilinear guide into the oropharynx region at least partially along the path of the guide; the guide comprising an elongate tube having a distal, proximal end and central aperture therebetween; the elongate tube being sized to allow insertion in a patient's mouth and advancement through an oropharynx region of the patient such that the distal end is located at or near a glottis of the patient while the proximal end is at or outside the patient's mouth; delivering a flexible bougie into the guide, the bougie sized with sufficient length, diameter and flexibility to navigate through the central aperture of elongate tube; wherein the elongate tube comprises a preformed curvilinear path corresponding to a natural curvature around a tongue region of the patient; the natural curvature having a first proximal curvilinear path corresponding to the tongue region and a second curvilinear path distal to and extending in a direction opposite the first curvilinear path to position and orient the distal end of the elongate tube at the glottis and in substantial alignment with a path of a tracheal segment distal of the glottis; and locating a distal end of the flexible bougie past the distal end of the guide and through the glottis to a region of the trachea.

17. The apparatus, system or method of any preceding or following embodiment: wherein the proximal end comprises a circular collar with a thumb notch and the elongate tube comprises a round profile allowing rotation within the patient; and wherein delivering a curvilinear guide comprises manual purchase of the proximal end for advancement and rotation of the elongate tube within the oropharynx region.

18. The apparatus, system or method of any preceding or following embodiment, wherein the notched circular collar provides visual and tactile indication of the angular orientation of the elongate tube with respect to the patient.

19. The apparatus, system or method of any of the preceding or subsequent embodiments, wherein the elongate tube has sufficient rigidity and the second curvilinear path is shaped with respect to the first curvilinear path such that the distal end naturally positions itself at a proper anterior-posterior location with respect to the glottis and such that an exit path of a distal end of the bougie when advanced past the distal end of the elongate tube is aligned with an opening of the glottis and orientation of the trachea.

20. The apparatus, system or method of any preceding or following embodiment: wherein the bougie comprises one or more markers at a location along its length corresponding to the length along the central aperture of the elongate tube; and wherein the one or more markers provide visualization that the distal end of a bougie is near, at or past the distal end of the elongate tube by some increment.

21. The apparatus, system or method of any preceding or following embodiment, further comprising: removing the guide while maintaining the position of the bougie in the patient; and installing an endotracheal tube over the bougie and delivering a distal end of the tube into the trachea.

22. The apparatus, system or method of any preceding or following embodiment, wherein the apparatus or system is connected to an oxygen source or breathing circuit.

23. The apparatus, system or method of any preceding or following embodiment, wherein the apparatus, system or method provides positive pressure ventilation to a patient.

As used herein, the singular terms "a," "an," and "the" may include plural referents unless the context clearly dictates otherwise. Reference to an object in the singular is not intended to mean "one and only one" unless explicitly so stated, but rather "one or more."

Phrasing constructs, such as "A, B and/or C", within the present disclosure describe where either A, B, or C can be present, or any combination of items A, B and C. Phrasing constructs indicating, such as "at least one of" followed by listing group of elements, indicates that at least one of these group elements is present, which includes any possible combination of these listed elements as applicable.

References in this specification referring to "an embodiment", "at least one embodiment" or similar embodiment wording indicates that a particular feature, structure, or characteristic described in connection with a described embodiment is included in at least one embodiment of the present disclosure. Thus, these various embodiment phrases are not necessarily all referring to the same embodiment, or to a specific embodiment which differs from all the other embodiments being described. The embodiment phrasing should be construed to mean that the particular features, structures, or characteristics of a given embodiment may be combined in any suitable manner in one or more embodiments of the disclosed apparatus, system or method.

As used herein, the term "set" refers to a collection of one or more objects. Thus, for example, a set of objects can include a single object or multiple objects.

As used herein, the terms "approximately", "approximate", "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for endotracheal intubation of a patient via a flexible bougie, the apparatus comprising:
    an elongate tube having a distal end and a proximal end;
    the elongate tube having a central aperture sized to receive a flexible bougie;
    the elongate tube being sized to allow insertion in a patient's mouth and advancement through an oropharynx region of the patient such that the distal end is located at or near a glottis of the patient while the proximal end is at or outside the patient's mouth;
    wherein the elongate tube comprises a pre-formed curvilinear path corresponding to a natural curvature around a tongue region of the patient;
    the natural curvature having a first proximal curvilinear path corresponding to the tongue region and a second curvilinear path distal to and extending in a direction opposite the first curvilinear path to position and orient the distal end of the elongate tube at the glottis and in substantial alignment with a path of a tracheal segment distal of the glottis;
    wherein the elongate tube comprises a non-reflective dark-colored plastic configured to minimize videoscopic glare.

2. The apparatus of claim 1, wherein the proximal end comprises a circular collar with a thumb notch allowing for manual purchase of the proximal end for advancement and rotation of the elongate tube within the oropharynx region.

3. The apparatus of claim 2, wherein the circular collar provides visual and tactile indication of an angular orientation of the elongate tube with respect to the patient.

4. The apparatus of claim 1, wherein the elongate tube has a round cross-section that promotes rotation of the elongate tube within the patient and tapers so that the central aperture is larger at the proximal end and smaller at the distal end.

5. The apparatus of claim 1, wherein the first proximal curvilinear path comprises a first radius and the second curvilinear path comprises a second radius smaller than the first radius.

6. The apparatus of claim 1, wherein the elongate tube has sufficient rigidity and the second curvilinear path is shaped with respect to the first curvilinear path such that the distal end naturally positions itself at a proper anterior-posterior location with respect to the glottis and such that an exit path of a distal end of the bougie when advanced past the distal end of the elongate tube is aligned with an opening of the glottis and orientation of the trachea.

7. A system for endotracheal intubation of a patient, the system comprising:
    a guide comprising an elongate tube having a distal end, a proximal end, and a central aperture between the distal end and the proximal end; and
    a flexible bougie sized with sufficient length, diameter and flexibility to navigate through the central aperture of elongate tube;
    the elongate tube being sized to allow insertion in a patient's mouth and advancement through an oropharynx region of the patient such that the distal end is located at or near a glottis of the patient while the proximal end is at or outside the patient's mouth;
    wherein the elongate tube comprises a pre-formed curvilinear path corresponding to a natural curvature around a tongue region of the patient;
    the natural curvature having a first proximal curvilinear path corresponding to the tongue region and a second curvilinear path distal to and extending in a direction opposite the first curvilinear path to position and orient the distal end of the elongate tube at the glottis and in substantial alignment with a path of a tracheal segment distal of the glottis;
    wherein the elongate tube comprises a non-reflective dark-colored plastic configured to minimize videoscopic glare.

8. The system of claim 7, wherein the proximal end comprises a circular collar with a thumb notch allowing for manual purchase of the proximal end for advancement and rotation of the elongate tube within the oropharynx region.

9. The system of claim 8, wherein the circular collar provides visual and tactile indication of an angular orientation of the elongate tube with respect to the patient.

10. The system of claim 7, wherein the elongate tube has a round cross-section that promotes rotation of the elongate tube within the patient and tapers so that the central aperture is larger at the proximal end and smaller at the distal end.

11. The system of claim 7, wherein the first proximal curvilinear path comprises a first radius and the second curvilinear path comprises a second radius smaller than the first radius.

12. The system of claim 7, wherein the elongate tube has sufficient rigidity and the second curvilinear path is shaped with respect to the first curvilinear path such that the distal end naturally positions itself at a proper anterior-posterior location with respect to the glottis and such that an exit path of a distal end of the bougie when advanced past the distal end of the elongate tube is aligned with an opening of the glottis and orientation of the trachea.

13. The system of claim 7:
    wherein the bougie comprises one or more markers at a location along its length corresponding to a length along the central aperture of the elongate tube; and
    wherein the one or more markers provide visualization that the distal end of a bougie is near, at or past the distal end of the elongate tube by some increment.

14. A method for endotracheal intubation of a patient using a pre-shaped, curvilinear guide via a flexible bougie under videoscopic visualization, the method comprising:
    delivering a video laryngoscope blade to a location within an oropharynx region of the patient;
    delivering a curvilinear guide into the oropharynx region at least partially along a path of the guide;
    the guide comprising an elongate tube having a distal end, a proximal end, and a central aperture between the distal end and the proximal end;
    the elongate tube being sized to allow insertion in a patient's mouth and advancement through an oropharynx region of the patient such that the distal end is located at or near a glottis of the patient while the proximal end is at or outside the patient's mouth;

delivering a flexible bougie into the guide, the bougie sized with sufficient length, diameter and flexibility to navigate through the central aperture of the elongate tube;

wherein the elongate tube comprises a pre-formed curvilinear path corresponding to a natural curvature around a tongue region of the patient;

the natural curvature having a first proximal curvilinear path corresponding to the tongue region and a second curvilinear path distal to and extending in a direction opposite the first curvilinear path to position and orient the distal end of the elongate tube at the glottis and in substantial alignment with a path of a tracheal segment distal of the glottis; and locating a distal end of the flexible bougie past the distal end of the guide and through the glottis to a region of the trachea.

15. The method of claim 14:

wherein the proximal end comprises a circular collar with a thumb notch and the elongate tube comprises a round profile allowing rotation within the patient; and wherein delivering a curvilinear guide comprises manual purchase of the proximal end for advancement and rotation of the elongate tube within the oropharynx region.

16. The method of claim 15, wherein the circular collar provides visual and tactile indication of an angular orientation of the elongate tube with respect to the patient.

17. The method of claim 14, wherein the elongate tube has sufficient rigidity and the second curvilinear path is shaped with respect to the first curvilinear path such that the distal end of the elongate tube naturally positions itself at a proper anterior-posterior location with respect to the glottis and such that an exit path of a distal end of the bougie when advanced past the distal end of the elongate tube is aligned with an opening of the glottis and orientation of the trachea.

18. The method of claim 14:

wherein the bougie comprises one or more markers at a location along its length corresponding to a length along the central aperture of the elongate tube; and wherein the one or more markers provide visualization that the distal end of the bougie is near, at or past the distal end of the elongate tube by some increment.

19. The method of claim 14, further comprising:

removing the guide while maintaining a position of the bougie in the patient; and installing an endotracheal tube over the bougie and delivering a distal end of the elongate tube into the trachea.

\* \* \* \* \*